(12) United States Patent
Uchida et al.

(10) Patent No.: US 6,485,847 B1
(45) Date of Patent: Nov. 26, 2002

(54) AMINE DERIVATIVE AND ORGANIC ELECTROLUMINESCENT DEVICE USING THE SAME

(75) Inventors: Manabu Uchida, Kanazawa (JP); Takenori Izumizawa, Kanazawa (JP); Kenji Furukawa, Kanagawa (JP)

(73) Assignee: Chisso Corporation, Osaka (JP)

(*) Notice: Subject to any disclaimer, the term of this patent is extended or adjusted under 35 U.S.C. 154(b) by 0 days.

(21) Appl. No.: 09/529,851

(22) PCT Filed: Oct. 20, 1998

(86) PCT No.: PCT/JP98/04730

§ 371 (c)(1),
(2), (4) Date: Jun. 26, 2000

(87) PCT Pub. No.: WO99/20596

PCT Pub. Date: Apr. 29, 1999

(30) Foreign Application Priority Data

Oct. 20, 1997 (JP) ............................................. 9-304988

(51) Int. Cl.$^7$ ............................................. H05B 33/14
(52) U.S. Cl. .................. 428/690; 428/917; 313/504; 313/506
(58) Field of Search .................. 428/690, 704, 428/917; 313/504, 506; 430/58.65, 58.75; 564/308, 429, 434

(56) References Cited

U.S. PATENT DOCUMENTS 5,047,687 A * 9/1991 VanSlyke .................... 313/503
5,061,569 A * 10/1991 VanSlyke et al. ........... 428/457
5,281,489 A * 1/1994 Mori et al. .................. 428/690

FOREIGN PATENT DOCUMENTS

| EP | 0 797 375 | * | 9/1997 |
| JP | 62-18566 | * | 1/1987 |
| JP | 62-201451 | * | 9/1987 |
| JP | 7-301927 | * | 11/1995 |
| JP | 9-255948 | * | 9/1997 |
| JP | 10-251633 | * | 9/1998 |

* cited by examiner

*Primary Examiner*—Marie Yamnitzky
(74) *Attorney, Agent, or Firm*—Sughrue Mion, PLLC

(57) ABSTRACT

An organic electroluminescent device contains a specific amine derivative represented by formula (1) as a hole-transportation material or light-emitting material, to thereby produce an organic EL device of high efficacy and prolonged service life.

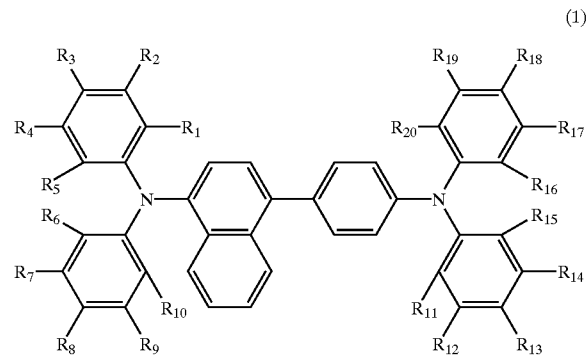

1 Claim, No Drawings

AMINE DERIVATIVE AND ORGANIC ELECTROLUMINESCENT DEVICE USING THE SAME

TECHNICAL FIELD

The present invention relates to an amine derivative used in an organic electroluminescent device and similar devices.

BACKGROUND ART

In recent years, an organic electroluminescent device (hereinafter abbreviated as "organic EL device") has become of interest as a candidate for a flat display of high luminance which has never been attained. In accordance with this trend, organic EL devices have been the subject of active research and development efforts. An organic EL device has a structure in which a light-emitting layer is sandwiched by two electrodes. Holes injected from a positive electrode and electrons injected from a negative electrode are recombined within the light-emitting layer, to thereby emit light. Organic materials used for producing an organic EL device include high- and low-molecular-weight materials, and both types of materials are known to provide an organic EL device which can emit light of high luminance.

Organic EL devices are categorized into two types. A first type contains a charge-transporting layer which transports electrons and/or holes and to which a fluorescent dye is added, as has been described by C. W. Tang et al. (Journal of the Applied Physics, 65, 3,610 (1989)). The other type employs a fluorescent dye singly in a light-emitting layer (for example, a device described in Japanese Journal of Applied Physics, 27, L269 (1988)).

Organic EL devices employing a fluorescent dye singly in a light-emitting layer are further classified into the following three types. A first type is directed to a three-layered device in which a light-emitting layer is sandwiched by a hole-transportation layer which transports only holes, which are a form of charge, and an electron-transportation layer, which transports only electrons. A second type is directed to a two-layered device in which a hole-transportation layer and a light-emitting layer are stacked. A third type is directed to a two-layered device in which an electron-transportation layer and a light-emitting layer are stacked. An organic EL device is known to have improved light-emitting efficacy when it has a two- or three-layered structure.

However, conventional, organic EL devices do not necessarily exhibit satisfactory performance in practical application. One major reason for this may be attributed to lack of durability of the material used in the devices, particularly hole-transportation material.

In addition, hole-transportation material used for conventional devices tends to combine with light-emitting material and electron-transportation material, which materials are also used for the devices, to thereby form an exciplex which yields poor device efficacy. Therefore, the types of light-emitting materials or electron-transportation materials which can be used have been limited.

A variety of materials centering on triphenylamine derivatives have been known as hole-transportation materials used for such organic EL devices, but few materials are suitable for practical use; i.e., few are materials which impose no limit on the types of other materials simultaneously used for the devices and which provide high light-emitting efficacy and long service life.

For example, there has been reported N,N'-diphenyl-N', N'-di(3-methylphenyl)-4,4'-diaminobiphenyl (hereafter abbreviated as TPD) (Applied Physics Letter, Vol. 57, No. 6, p. 531, 1990). This compound is thermally unstable, and is disadvantageous in terms of the service life of the resultant device. Many other triphenylamine derivatives are disclosed in U.S. Pat. Nos. 5,047,687, 4,047,948, and 4,536,457 and in Japanese Patent Application Laid-Open (kokai) Nos. 5-239455 and 8-87122. However, none of these are satisfactory in terms of well-balanced characteristics in practical application.

In addition, star-burst amine derivatives disclosed in Japanese Patent Application Laid-Open (kokai) Nos. 4-308688 and 6-1972 and "Advanced Materials" Vol. 6, p. 677 (1994); and compounds disclosed in Japanese Patent Application Laid-Open (kokai) Nos. 7-126226, 7-126615, 7-331238, 7-97355, 8-48656, and 8-100172 and, "Journal of the Chemical Society Chemical Communication" p. 2175 (1996) are unsatisfactory in terms of characteristics in practical application; i.e., they impose limitation of the types of other materials which is used simultaneously and fail to attain high light-emitting efficacy and long service life.

Incidentally, Japanese Patent Application Laid-Open (kokai) No. 7-301927 discloses that a naphthylamine derivative is applied to electrophotography, but does not disclose application of the derivative to an organic EL device.

As described above, hole-transportation materials used in conventional organic EL devices do not exhibit satisfactory performance in practical application, and thus there is need for an excellent material that can enhance the light-emitting efficacy and service life of organic EL devices.

In order to solve the above-described problems, an object of the present invention is to provide an organic EL device which has high light-emitting efficacy and long service life, and a novel hole-transportation material and light-emitting material which are used in the EL device and which are not limited by other materials used simultaneously.

DISCLOSURE OF THE INVENTION

In view of the foregoing, the present inventors have conducted extensive studies in an attempt to solve the aforementioned problems involved in conventional organic EL devices, and have found that when a specific type of amine derivative is used, a resultant organic EL device has high light-emitting efficacy and long service life. The present invention has been accomplished on the basis of this finding.

Accordingly, in a first aspect of the present invention, there is provided a specific amine compound represented by the following formula (1):

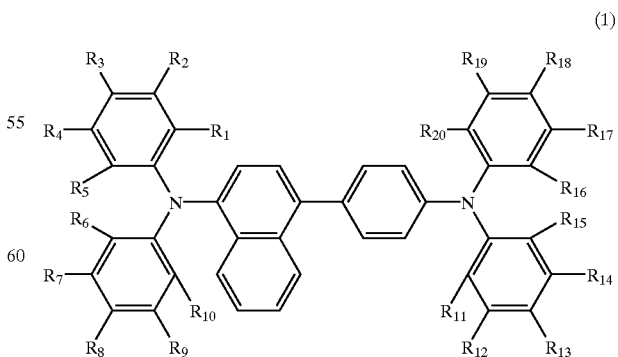

(1)

[wherein each of $R_1$ to $R_{20}$ represents a hydrogen atom, a halogen atom, a C1–C6 alkyl group, a C1–C6 alkoxy group, a substituted or unsubstituted amino group, a substituted or unsubstituted aryl group, or a substituted or unsubstituted heterocyclic group, and any of the substituted or unsubstituted aryl group or any of the substituted or unsubstituted heterocyclic group may form a condensed structure].

In a second aspect of the present invention, there is provided an organic electroluminescent device comprising an amine derivative represented by formula (1).

In a third aspect of the present invention, there is provided an organic electroluminescent device comprising a hole-transportation layer which contains an amine derivative represented by formula (1).

In a fourth aspect of the present invention, there is provided an organic electroluminescent device comprising a light-emitting layer which contains an amine derivative represented by formula (1).

In a fifth aspect of the present invention, there is provided an organic electroluminescent device comprising a hole-injection layer which contains an amine derivative represented by formula (1).

In a sixth aspect of the present invention, there is provided a hole-transportation material comprising an amine derivative represented by formula (1).

In a seventh aspect of the present invention, there is provided a light-emitting material comprising an amine derivative represented by formula (1).

BEST MODES FOR CARRYING OUT THE INVENTION

The present invention will next be described in detail.

As described above, the organic EL device of the present invention comprises an amine derivative represented by formula (1), and the amine derivative mainly functions as a hole-transportation material, a light-emitting material, and/or a hole-injection material. The amine derivative per se may form one or more of a hole-transportation layer, a light-emitting layer, and a hole-injection layer, or may be contained in one or more of these layers.

The organic EL device of the present invention may be realized in a variety of modes. The device has a basic structure in which a layer containing an amine derivative represented by formula (1) is sandwiched by a pair of electrodes (a positive electrode and a negative electrode), and a hole-injection material, a hole-transportation material, a light-emitting material, an electron-injection material, or an electron-transportation material may optionally be incorporated into the amine-derivative-containing layer. Alternatively, a hole-injection layer, a hole-transportation layer, a light-emitting layer, an electron-injection layer, or an electron-transportation layer containing these materials may be formed other than the amine-derivative-containing layer.

Specific structural examples of the organic EL device of the present invention include stacked-layer structures such as (1) positive electrode/layer containing an amine derivative of the present invention/negative electrode; (2) positive electrode/layer containing an amine derivative of the present invention/light-emitting layer/negative electrode; (3) positive electrode/layer containing an amine derivative of the present invention/light-emitting layer/electron-injection layer/negative electrode; (4) positive electrode/hole-injection layer/layer containing an amine derivative of the present invention/light-emitting layer/electron-injection layer/negative electrode; (5) positive electrode/layer containing an amine derivative of the present invention/hole-transportation layer/light-emitting layer/electron-injection layer/negative electrode; and (6) positive electrode/hole-injection layer/layer containing an amine derivative of the present invention/electron-injection layer/negative electrode. The structure of the organic EL device is not limited thereto.

In the above cases, a hole-injection layer and an electron-injection layer are not always necessary, but provision of these layers further enhances light-emitting efficacy of the EL device.

When a layer containing an amine derivative of the present invention is used as a light-emitting layer, addition of another light-emitting material may change the color of emitted light and enhance light-emitting efficacy of the organic EL device.

The organic EL device of the present invention, having any of the structures listed above, is preferably supported by a substrate. No particular limitation is imposed on the material of the substrate, and conventionally used material for the substrate of an organic EL device; for example, glass, transparent plastic, conductive polymer, or quartz, may be used.

Each layer of the organic EL device of the present invention may be produced by subjecting a material of the layer to a conventional processing method; for example, a vapor deposition method, a spin-coating method, or a casting method, to thereby form a thin film.

No particular limitation is imposed on the thickness of the thus-formed layer; for example, a light-emitting layer. The thickness may be arbitrarily chosen, and is usually chosen from a range of 2 nm–5,000 nm.

With regard to materials of the positive electrode in the organic EL device of the present invention, there may preferably be used a metal, an alloy, an electrically conductive compound, or a mixture thereof having a work function of 4 eV or more.

Specific examples of the positive electrode materials include metals such as Au; and dielectric transparent materials such as CuI, indium tin oxide (hereinafter abbreviated as ITO), $SnO_2$, and ZnO.

The positive electrode may be produced by subjecting the aforementioned material to vapor deposition or sputtering to thereby form a thin film.

In order to attain emission from the positive electrode, the percent transmission of the positive electrode is preferably 10% or more, and the sheet resistance of the positive electrode is preferably some hundreds Ω/mm or less. The thickness of the positive electrode, which depends on the material, is usually determined within a range of 10 nm–1 µm, preferably 10–400 nm.

With regard to materials of the negative electrode, there may preferably be used a metal, an alloy, an electrically conductive compound, or a mixture thereof having a work function of 4 eV or less. Specific examples of the negative electrode materials include calcium, magnesium, lithium, aluminum, magnesium alloys, lithium alloys, aluminum alloys, aluminum/lithium mixtures, magnesium/silver mixtures, and indium.

The negative electrode may be produced by subjecting the aforementioned material to vapor deposition or sputtering to thereby form a thin film. The sheet resistance of the negative electrode is preferably some hundreds Ω/mm or less. The thickness of the negative electrode is usually determined within a range of 10 nm–1 µm, preferably 50–200 nm.

In the organic EL device of the present invention, either or both of the positive electrode and the negative electrode are preferably transparent or semi-transparent so as to enhance output efficacy of emission through the EL device.

As described above, the organic EL device of the present invention may be realized in a variety of modes. In the organic EL device of each mode, a hole-injection layer or hole-transportation layer comprises a hole-transmission compound, and has a function of transmitting to a light-emitting layer holes injected from a positive electrode. Therefore, when the hole-injection layer or hole-transportation layer is provided between the positive electrode and the light-emitting layer, a large amount of holes are injected to the light-emitting layer at a lower electrical field. In addition, electrons injected from a negative electrode or electron-injection layer can be confined in the light-emitting layer, to thereby enhance light-emitting efficacy. Thus, the obtained organic EL device can exhibit excellent light-emitting performance.

The amine derivative used in the organic EL device of the present invention exhibits excellent ability to inject and transport holes, and to confine electrons. Therefore, the organic EL device of the present invention exhibits high light-emitting efficacy.

Specific examples of the amine derivative of the present invention include compounds represented by the following formulas (2) through (15).

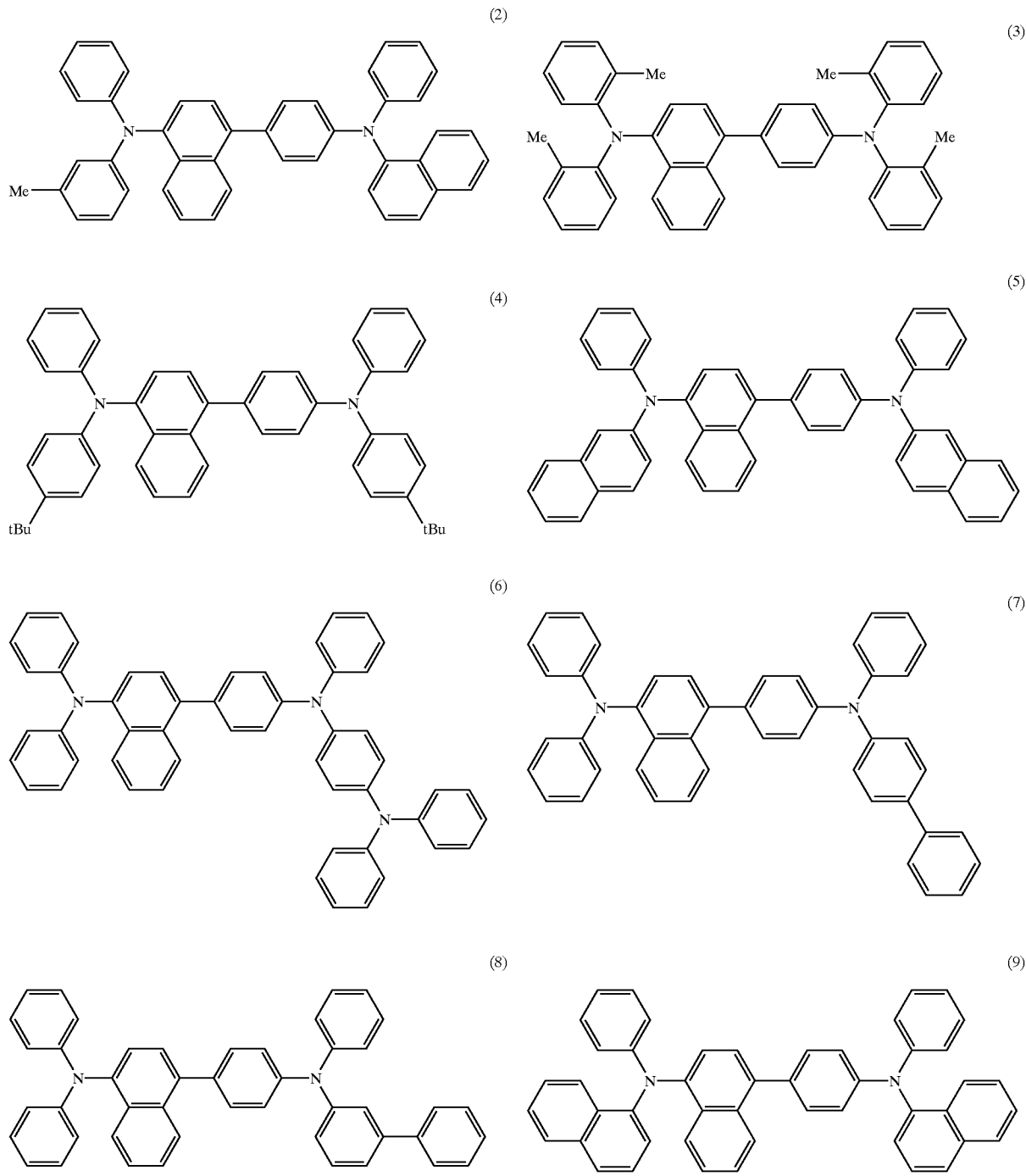

-continued
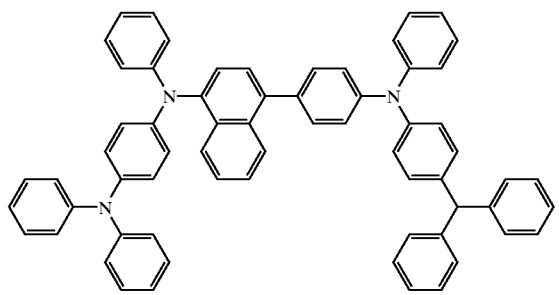
(10)
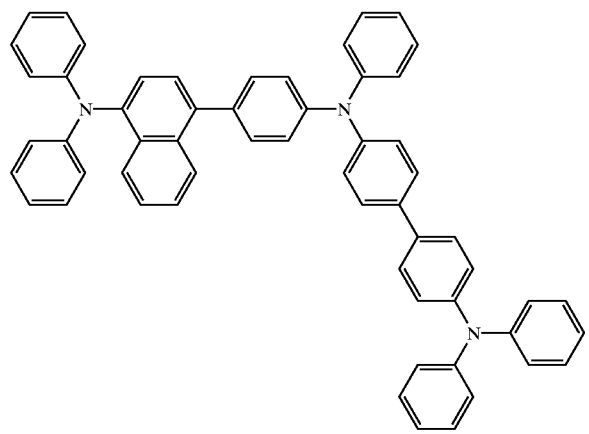
(11)
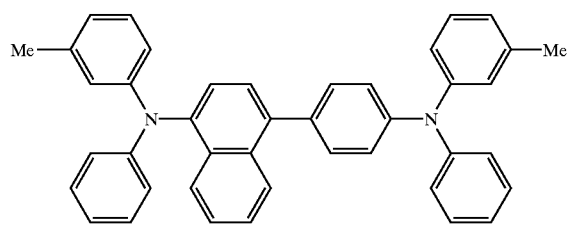
(12)
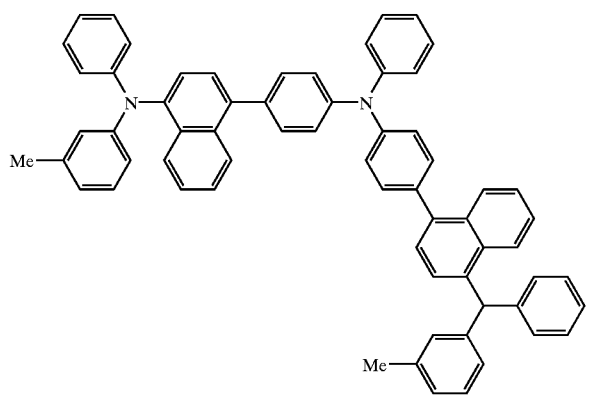
(13)
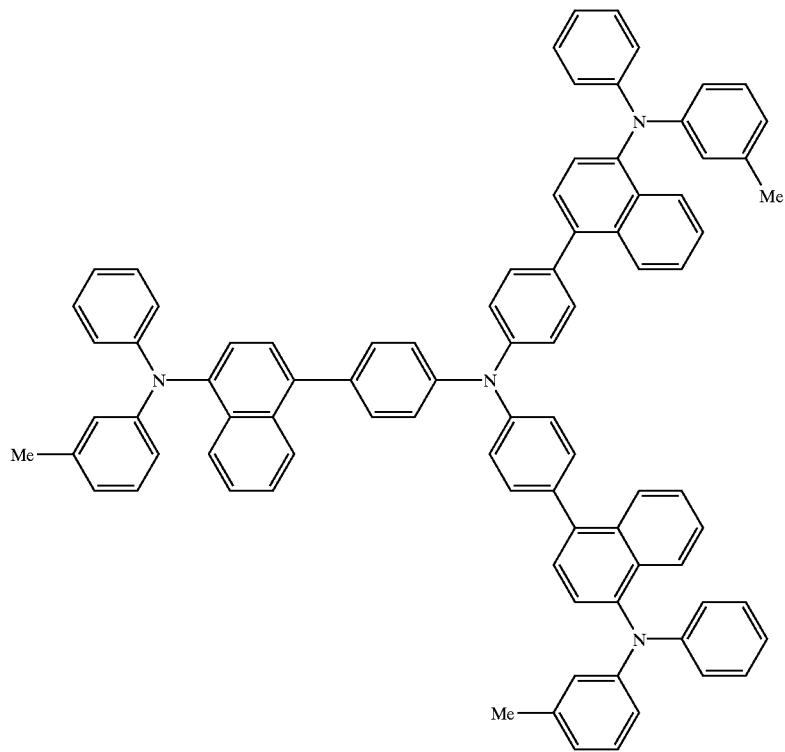
(14)

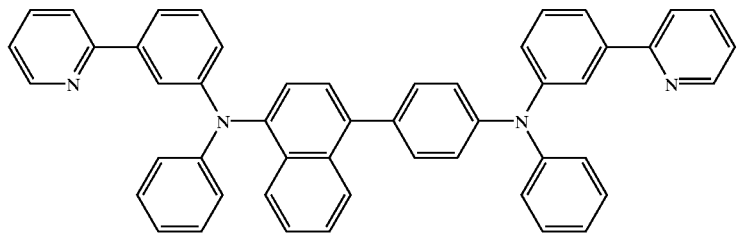

(15)

These compounds may be synthesized through a known synthesis method; for example, any of the methods described in Examples of the present specification. Specifically, a metallic reagent such as alkyllithium is added to a solution of triarylamine halide at low temperature in an inert gas atmosphere, and the resultant mixture is stirred. Subsequently, zinc chloride or a similar compound is further added to the mixture, and the resultant mixture is stirred for replacement of the metallic reagent with a metallic reagent which promotes a coupling reaction. A solution of another triarylamine halide and a coupling catalyst such as dichlorobis(triphenylphosphine)palladium are added to the resultant mixture for reaction, to thereby obtain the compound of the present invention. No particular limitation is imposed on the type of inert gas which is used herein, so long as the gas does not impede the reaction. For example, nitrogen gas or argon gas may be used. Examples of metallic reagents which may be used include n-butyllithium, sec-butyllithium, tert-butyllithium, phenyllithium, lithium, and magnesium. No particular limitation is imposed on the reaction temperature, and the reaction is usually carried out at a temperature within a range of −150° C. to 100° C., preferably −100° C. to room temperature. Examples of metals which promote a coupling reaction include magnesium, tin, zinc, and boron. A coupling catalyst is preferably a metal complex of palladium or nickel. No particular limitation is imposed on the type of reaction solvent, so long as the solvent does not impede the reaction, and an ether solvent such as diethyl ether, butyl methyl ether, or tetrahydrofuran (hereinafter abbreviated as THF) is usually used.

With regard to a hole-injection material and hole-transportation material that are used in the organic EL device of the present invention, there may be used an arbitrary material selected from materials which have conventionally been used as charge-transportation materials for holes among photoconductive materials and from known materials which are used in a hole-injection layer or a hole-transportation layer of an organic EL device.

Examples of such materials include carbazole derivatives (e.g., N-phenylcarbazole and polyvinylcarbazole); triarylamine derivatives (e.g., TPD, polymers having an aromatic tertiary amine in a main or side chain, 1,1-bis(4-di-p-tolylaminophenyl)cyclohexane, N,N'-diphenyl-N,N'-dinaphthyl-4,4'-diaminobiphenyl, 4,4',4"-tris{N-(3-methylphenyl)-N-phenylamino}triphenylamine, a compound described in "Journal of the Chemical Society Chemical Communications" p. 2175 (1996), compounds disclosed in Japanese Patent Application Laid-Open (kokai) Nos. 57-144558, 61-62038, 61-124949, 61-134354, 61-134355, 61-112164, 4-308688, 6-312979, 6-267658, 7-90256, 7-97355, 6-1972, 7-126226, 7-126615, 7-331238, 8-100172, and 8-48656, and a star-burst amine derivative described in "Advanced Materials" Vol. 6, p. 677 (1994)); stilbene derivatives (e.g., a compound described in Proceedings (II) of the 72nd annual spring convention of The Chemical Society of Japan, p. 1392, 2PB098); phthalocyanine derivatives (e.g., metal-free phthalocyanine, copper phthalocyanine); and polysilane.

Each of a hole-injection layer and a hole-transportation layer of the organic EL device of the present invention may be formed of a single layer containing at least one species of the above-described compounds, or may be formed of a plurality of hole-injection layers laminated one on another, in which the layers contain different species of the compounds.

The amine derivative of the present invention is suitable for use as a light-emitting material, due to introduction of a phenylnaphthylene group. In particular, the amine derivative emits blue light, and the emission color of the organic EL device may be changed by incorporation of another light-emitting material of blue, green, or red color.

Incidentally, a compound used in a layer that constitutes the organic EL device of the present invention preferably forms no exciplex with a compound used in another layer. The amine derivative of the present invention has an advantage in that it rarely forms an exciplex with another compound. This is considered to be attributed to introduction of a phenylnaphthylene group.

In the organic EL device of the present invention of each mode, an electron-transportation layer comprises an electron-transmission compound, and has a function of transmitting to a light-emitting layer electrons injected from a negative electrode.

No particular limitation is imposed on the type of electron-transmission compound, and an employed compound may be arbitrarily selected from known compounds. Examples of such preferred electron-transmission compounds include diphenylquinone derivatives (e.g., those described in *Denshi-Shashin Gakkai-shi*, 30, 3 (1991)); perylene derivatives (e.g., those described in J. Apply. Phys., 27, 269 (1988)); oxadiazole derivatives (e.g., those described in the above-described literature, Jpn. J. Appl. Phys., 27, L713 (1988), or Appl. Phys. Lett., 55, 1489 (1989)); thiophene derivatives (e.g., those disclosed in Japanese Patent Application (kokai) No. 4-212286); triazole derivatives (e.g., those described in Jpn. J. Appl. Phys., 32, L917 (1993)); thiadiazole derivatives (e.g., those described in the 43rd Proceedings of The Society of Polymer Science, Japan, (III) Pla007); metal complexes of an oxine derivative (e.g., those described in the technical research report of *Denshi Joho Tsushin Gakkai*, 92 (311), 43 (1992)); polymers of quinoxaline derivative (e.g., those described in Jpn. J. Appl. Phys., 33, L250 (1994)); and phenanthroline derivatives (e.g., those described in the 43rd Proceedings of *Kobunshi Toronkai*, 14J07).

With regard to other light-emitting materials used in the organic EL device of the present invention, there may be used known light-emitting materials, such as daylight fluorescent materials, fluorescent brighteners, laser dyes, organic scintillators, and reagents for fluorescent analysis, as described in "*Hikari Kino Zairyo*" in *Kobunshi Kino Zairyo* series, published by Kyoritsu Shuppan (1991), P236, edited by The Society of Polymer Science, Japan.

Specifically, examples of preferred light-emitting materials include polycondensed ring compounds such as anthracene, phenanthrene, pyrene, chrysene, perylene, coronene, rubrene, and quinacridone; oligophenylene compounds such as quaterphenyl; scintillators for liquid scintillation such as 1,4-bis(2-methylstyryl)benzene, 1,4-bis(4-methylstyryl)benzene, 1,4-bis(4-methyl-5-phenyl-2-oxazolyl)benzene, 1,4-bis(5-phenyl-2-oxazolyl)benzene, 2,5-bis(5-tert-butyl-2-benzoxazolyl)thiophene, 1,4-diphenyl-1,3-butadiene, 1,6-diphenyl-1,3,5-hexatriene, or 1,1,4,4-tetraphenyl-1,3-butadiene; a metal complex of an oxine derivative disclosed in Japanese Patent Application (kokai) No. 63-264692; coumarin dyes; dicyanomethylenepyran dyes; dicyanomethylenethiopyran dyes; polymethine dyes; oxobenzanthracene dyes; xanthene dyes; carbostyryl dyes; perylene dyes; an oxazine compound disclosed in German Patent No. 2534713; a stilbene derivative described in the Proceedings of the 40th Joint Lecture of Applied Physics, 1146 (1993); a spiro compound disclosed in Japanese Patent Application (kokai) No. 7-278537; and an oxadiazole compound disclosed in Japanese Patent Application (kokai) No. 4-363891.

An example preferred method for producing an organic EL device by use of the amine derivative of the present invention will next be described. Specifically, a method for producing an organic EL device formed of the above-described positive electrode/layer containing the amine derivative of the present invention/negative electrode will be described. A thin film comprising a desired electrode substance; for example, a positive electrode substance, is formed on an appropriate substrate through vapor disposition of sputtering so as to attain a film thickness; of 1 µm or less, preferably 10–200 nm, to thereby form a positive electrode. Subsequently, a thin film comprising the amine derivative is formed on the positive electrode.

In order to form a thin film of the amine derivative, a spin-coating method, a casting method, or a vapor deposition method may be employed. Of these methods, a vapor deposition method is preferably employed in consideration that a homogeneous film is easy to produce and the film is not prone to generation of pinholes.

When a thin film is formed through vapor deposition, the desirable vapor deposition conditions are typically determined within the following ranges: boat heating temperature of 50–400° C., degree of vacuum of $10^{-6}$–$10^{-3}$ Pa, vapor deposition rate of 0.01–50 nm/sec, substrate temperature of −150 to +300° C., and film thickness of 5 nm to 5 µm, in accordance with the species of amine derivatives used in a layer containing an amine derivative and the desired crystal structure and association state of a molecular accumulated film.

After completion of formation of a layer containing the amine derivative, a thin film comprising a substance for forming a negative electrode is formed on the layer through vapor deposition or sputtering, so as to attain a film thickness of 1 µm or less, to thereby produce a negative electrode. Thus, a desired organic EL device is obtained.

Alternatively, in production of the above-described organic EL device, the procedure may be performed in the reverse manner; i.e., successively forming a negative electrode, a light-emitting layer, and a positive electrode, in this sequence.

DC voltage is applied to the thus-obtained organic EL device, with polarity such that the positive electrode has positive (+) potential and the negative electrode has negative (−) potential. When the application voltage is approximately 2–40 V, emission is observed from a transparent or semi-transparent electrode (either the positive electrode, the negative electrode, or both).

The organic EL device of the present invention emits light when AC voltage is applied thereto. The applied AC voltage may have an arbitrary waveform.

As described above, the organic EL device of the present invention exhibits not only high light-emitting efficacy but also excellent durability during storage and in use. This is because the amine derivative of the present invention has a glass transition point (hereinafter abbreviated as Tg). The organic EL device of the present invention preferably comprises an amine derivative having a Tg of 80° C. or higher, more preferably a compound having a Tg of 100° C. or higher.

In general, each of layers constituting an organic EL device is amorphous, and crystallization of the layer may result in breakage of the organic EL device. Thus, a material having a high Tg is preferably used in an organic EL device. For example, N-phenyl-N-(3-methylphenyl)-4-{4-(N-phenyl-N-naphthyl)aminophenyl}naphthylamine represented by the aforementioned formula (2) (hereinafter abbreviated as PMPNAPN), an example of the amine derivative of the present invention, has a Tg of 107° C., which is approximately 40° C. higher than that of TPD.

A display apparatus comprising an organic EL device may be used or stored in a high-temperature location; for example, in a greenhouse or car, or in a location exposed to direct sunlight. In order to endure such harsh conditions, a material having a high Tg is used in an organic EL device, to thereby prolong the service life of the device.

EXAMPLES

The present invention will next be described in more detail by way of examples, which should not be construed as limiting the invention thereto.

[Method for Measuring Tg]

Tg was measured through DSC. A sample was melted and quenched to assume a glass state. Subsequently, the temperature of the sample was elevated at a rate of 40° C./minute.

Example 1

Synthesis of PMPNAPN [Compound of Formula (2)]

A 1.6 mol/l solution (1.7 ml) of butyllithium in hexane was added dropwise to a THF solution (5 ml) containing N-phenyl-N-(3-methylphenyl)-(4-bromo-1-naphthyl)amine (900 mg), at −78° C. in a nitrogen atmosphere. After the mixture was stirred for 15 minutes, a tetramethylethylenediamine complex of zinc chloride (640 mg) was added to the mixture, and the resultant mixture was stirred for 30 minutes at room temperature. Subsequently, a THF solution (5 ml) containing N-phenyl-N-(1-naphthyl)-N-(4-bromophenyl)amine (1 g), and bistriphenylphosphinepalladium (50 mg) were added to the mixture, and the resultant mixture was heated and refluxed for 19 hours. After the mixture was allowed to cool, water and toluene were added, to thereby obtain a crude product in an organic layer through extraction. After concentration under reduced pressure, the product was purified by silica gel column chromatography (heptane/ toluene=5/1), to thereby obtain 0.2 g of the title compound. The fluorescent color of the compound in toluene was violet.

$^1$H-NMR (CDCl$_3$) δ=2.23 (s, 3H), 6.7–7.6 (m, 26H), 7.81 (d, 1H), 7.91 (d, 1H), 8.0–8.04 (m, 3H).

The Tg of the thus-obtained PMPNAPN, as measured through DSC, was 107° C.

Example 2

Synthesis of 4,4'-bis[4"-{N-phenyl-N-(3'''-methylphenyl)amino}naphthyl]triphenylamine [Compound of Formula (13)] (Hereinafter Abbreviated as BPMANT)

The procedure of Example 1 was repeated, except that N-phenyl-N-(1-naphthyl)-N-(4-bromophenyl)amine was replaced by 4,4'-dibromotriphenylamine, to thereby synthesize the title compound.

$^1$H-NMR (CDCl$_3$) δ=2.24 (s, 6H), 6.7–7.6 (m, 39H), 8.0–8.1 (m, 4H).

The Tg of the thus-obtained BPMANT, as measured through DSC, was 145° C.

Example 3

Synthesis of 4,4',4"-tris[4'''-{N-phenyl-N-(3''''-methylphenyl)amino}naphthyl]triphenylamine [Compound of Formula (14)] (Hereinafter Abbreviated as TPMANT)

The procedure of Example 1 was repeated, except that N-phenyl-N-(1-naphthyl)-N-(4-bromophenyl)amine was replaced by 4,4',4"-triiodotriphenylamine, to thereby synthesize the title compound.

$^1$H-NMR (CDCl$_3$) δ=2.25 (s, 9H), 6.78 (bd, 3H), 6.8–7.0 (m, 9H), 7.60 (bd, 6H), 7.11 (t, 3H), 7.2 (m, 6H), 7.3–7.6 (m, 24H), 8.06 (bd, 3H), 8.12 (bd, 3H).

The Tg of the thus-obtained TPMANT, as measured through DSC, was 168° C.

Example 4

A glass substrate (25 mm×75 mm×1.1 mm, product of Tokyo Sanyoshinku) onto which ITO had been vapor-deposited so as to attain a film thickness of 50 nm was used as a transparent support substrate. The support substrate was fixed upon a substrate holder of a commercially available vapor deposition apparatus (product of Shinkukiko). A quartz crucible containing PMPNAPN and another quartz crucible containing tris(8-hydroxyquinoline)aluminum (hereinafter abbreviated as Alq) were placed in a vacuum vessel, and the internal pressure of the vessel was reduced to 1×10$^{-4}$ Pa.

The crucible containing PMPNAPN was heated for vapor deposition of PMPNAPN on the support substrate, so as to form a film having a thickness of 50 nm. Then, the crucible containing Alq was heated for vapor deposition of Alq, so as to form a film having a thickness of 50 nm. The vapor deposition rates were 0.1–0.2 nm/sec.

Subsequently, the internal pressure of the vacuum vessel was reduced to 2×10$^{-4}$ Pa. Magnesium placed in a graphite crucible was vapor-deposited at a deposition rate of 1.2–2.4 nm/sec, and simultaneously, silver placed in another crucible was vapor-deposited at a deposition rate of 0.1–0.2 nm/sec, to thereby form an Mg—Ag mixture metal electrode (200 nm), which serves as a counter electrode, on a light-emitting layer, to thereby form a. Thus, an organic EL device was produced.

In the thus-produced organic EL device, when a DC voltage of 5 V was applied between the ITO electrode serving as a positive electrode and the Mg—Ag mixture electrode serving as a negative electrode, a current of about 5 mA/cm$^2$ flowed and green light having a wavelength of 530 nm was emitted with a luminance of 100 cd/m$^2$.

Example 5

The procedure of Example 4 was repeated, except that PMPNAPN was replaced by BPMANT, to thereby produce an organic EL device.

In the thus-produced organic EL device, when a DC voltage of 5 V was applied between the ITO electrode serving as a positive electrode and the Mg—Ag mixture electrode serving as a negative electrode, a current of about 5 mA/cm$^2$ flowed and green light was emitted with a luminance of 130 cd/m$^2$.

Example 6

The procedure of Example 4 was repeated, except that PMPNAPN was replaced by TPMANT, to thereby produce an organic EL device.

In the thus-produced organic EL device, when a DC voltage of 5 V was applied between the ITO electrode serving as a positive electrode and the Mg—Ag mixture electrode serving as a negative electrode, a current of about 3 mA/cm$^2$ flowed and green light was emitted with a luminance of 70 cd/m$^2$.

Example 7

In the same manner as in Example 4, a transparent support substrate was fixed upon a substrate holder of a vapor deposition apparatus. A quartz crucible containing PMPNAPN, another crucible containing TPD, and still another crucible containing Alq were placed in a vacuum vessel, and the internal pressure of the vessel was reduced to 1×10$^{-4}$ Pa.

The crucible containing PMPNAPN was heated for vapor deposition of PMPNAPN on the support substrate, so as to form a film having a thickness of 30 nm. Then, the crucible containing TPD was heated for vapor deposition of TPD, so as to form a film having a thickness of 20 nm. Furthermore, the crucible containing Alq was heated for vapor deposition of Alq, so as to form a film having a thickness of 50 nm. The vapor deposition rates were 0.1–0.2 nm/sec.

Subsequently, the internal pressure of the vacuum vessel was reduced to 2×10$^{-4}$ Pa. Magnesium placed in a graphite crucible was vapor-deposited at a deposition rate of 1.2–2.4 nm/sec, and simultaneously, silver placed in another crucible was vapor-deposited at a deposition rate of 0.1–0.2 nm/sec, to thereby form an Mg—Ag mixture metal electrode (200 nm), which serves as a counter electrode, on a light-emitting layer under the above-described conditions. Thus, an organic EL device was produced.

In the thus-produced organic EL device, when a DC voltage of 5 V was applied between the ITO electrode serving as a positive electrode and the Mg—Ag mixture electrode serving as a negative electrode, a current of about 7 mA/cm$^2$ flowed and green light was emitted with a luminance of 180 cd/m$^2$.

Example 8

In the same manner as in Example 4, a transparent support substrate was fixed upon a substrate holder of a vapor deposition apparatus. A quartz crucible containing PMPNAPN, another crucible containing TPD, and another crucible containing 9,9'-spirobisilafluorene were placed in a vacuum vessel, and the internal pressure of the vessel was reduced to $1 \times 10^{-4}$ Pa.

The crucible containing TPD was heated for vapor deposition of TPD on the support substrate, so as to form a film having a thickness of 50 nm. Then, the crucible containing PMPNAPN was heated for vapor deposition of PMPNAPN, so as to form a film having a thickness of 20 nm. Furthermore, the crucible containing 9,9'-spirobisilafluorene was heated for vapor deposition of 9,9'-spirobisilafluorene thereon, so as to form a film having a thickness of 50 nm. The vapor deposition rates were 0.1–0.2 nm/sec.

Subsequently, the internal pressure of the vacuum vessel was reduced to $2 \times 10^{-4}$ Pa. Magnesium placed in a graphite crucible was vapor-deposited at a deposition rate of 1.2–2.4 nm/sec, and simultaneously, silver placed in another crucible was vapor-deposited at a deposition rate of 0.1–0.2 nm/sec, to thereby form an Mg—Ag mixture metal electrode (200 nm), which serves as a counter electrode, on a light-emitting layer under the above-described conditions. Thus, an organic EL device was produced.

In the thus-produced organic EL device, when a DC voltage of 7 V was applied between the ITO electrode serving as a positive electrode and the Mg—Ag mixture electrode serving as a negative electrode, a current of about 5 mA/cm$^2$ flowed and blue light was emitted from PMPNAPN.

Example 9

In the same manner as in Example 4, a transparent support substrate was fixed upon a substrate holder of a vapor deposition apparatus. A quartz crucible containing PMPNAPN, another crucible containing 4,4',4''-tris{N-(3-methylphenyl)-N-phenylamino}triphenylamine, and still another crucible containing 2,5-bis{5-(2-benzo[b]thienyl)thienyl}-1,1,3,4-tetraphenylsilacyclopentadiene were placed in a vacuum vessel, and the internal pressure of the vessel was reduced to $1 \times 10^{-4}$ Pa.

The crucible containing 4,4',4''-tris{N-(3-methylphenyl)-N-phenylamino}triphenylamine was heated for vapor deposition thereof on the support substrate, so as to form a film having a thickness of 30 nm. Then, the crucible containing PMPNAPN was heated for vapor deposition of PMPNAPN, so as to form a film having a thickness of 20 nm. Furthermore, the crucible containing 2,5-bis{5-(2-benzo[b]thienyl)thienyl}-1,1,3,4-tetraphenylsilacyclopentadiene was heated for vapor deposition thereof, so as to form a film having a thickness of 50 nm. The vapor deposition rates were 0.1–0.2 nm/sec.

Subsequently, the internal pressure of the vacuum vessel was reduced to $2 \times 10^{-4}$ Pa. Magnesium placed in a graphite crucible was vapor-deposited at a deposition rate of 1.2–2.4 nm/sec, and simultaneously, silver placed in another crucible was vapor-deposited at a deposition rate of 0.1–0.2 nm/sec, to thereby form an Mg—Ag mixture metal electrode (200 nm), which serves as a counter electrode, on a light-emitting layer under the above-described conditions. Thus, an organic EL device was produced.

In the thus-produced organic EL device, when a DC voltage of 15 V was applied between the ITO electrode serving as a positive electrode and the Mg—Ag mixture electrode serving as a negative electrode, a current of about 100 mA/cm$^2$ flowed and red light was emitted.

Comparative Example 1

The Tg of TPD, as measured through DSC, was 69° C.

Comparative Example 2

The procedure of Example 4 was repeated, except that PMPNAPN used in Example 4 was replaced by TPD, to thereby produce an organic EL device.

In the thus-produced organic EL device, when DC voltage was applied between the ITO electrode serving as a positive electrode and the Mg—Ag mixture electrode serving as a negative electrode at 100° C., light was extinguished after several seconds. In contrast, when DC voltage was applied to the organic EL device produced in Example 4 at 100° C., light was emitted even after one hour.

INDUSTRIAL APPLICABILITY

The amine derivative of the present invention has a high Tg and exhibits excellent hole-transportation performance, and is thus suitable for producing a transportation layer of an organic EL device or for electrophotography. Furthermore, the derivative rarely forms an exciplex between light-emitting and electron-transportation materials, and thus the derivative can be combined with various materials to thereby produce an organic EL device which maintains light-emitting efficacy and emits light of different colors. In addition, the derivative has high light-emitting efficacy and is suitable as a light-emitting material.

The organic EL device of the present invention comprises the above-described amine derivative, and has high light-emitting efficacy and prolonged service life. In addition, a full-colored display is realized by use of the device. Accordingly, use of the organic EL device of the present invention enables production of a full-colored display of prolonged service life.

What is claimed is:

1. An organic electroluminescent device comprising an amine derivative represented by the following formula (1):

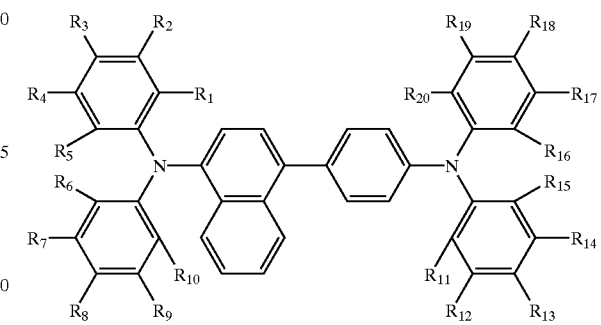

(1)

wherein each of $R_1$ to $R_{20}$ represents a hydrogen atom, a halogen atom, a $C_1$–$C_6$ alkyl group, a $C_1$–$C_6$ alkoxy group, a substituted or unsubstituted amino group, a substituted or unsubstituted aryl group, or a substituted or unsubstituted heterocyclic group, and any of the substituted or unsubstituted aryl group or any of the substituted or unsubstituted heterocyclic group may form a condensed structure, wherein said electroluminescent device comprises a layer containing the amine derivative represented by the formula (1) sandwiched between a pair of electrodes, which layer is a light-emitting layer which contains the amine derivative represented by formula (1) as a light-emitting compound.

* * * * *